(12) United States Patent
Yang et al.

(10) Patent No.: US 10,493,418 B2
(45) Date of Patent: Dec. 3, 2019

(54) MICROCAPSULE MATERIAL CAPABLE OF REDUCING POLLUTION CONTAINING POLYCYCLIC AROMATIC HYDROCARBON, AND PREPARATION METHOD AND APPLICATION THEREOF

(71) Applicants: South China University of Technology, Guangzhou (CN); Guangdong Yue Gang Water Supply Co. Ltd., Shenzhen (CN)

(72) Inventors: Chen Yang, Guangzhou (CN); Zhi Dang, Guangzhou (CN); Fucai Deng, Guangzhou (CN); Guosheng Sun, Guangzhou (CN); Huixing Huang, Guangzhou (CN); Chuling Guo, Guangzhou (CN); Guining Lu, Guangzhou (CN); Xiaoyun Yi, Guangzhou (CN)

(73) Assignees: South China University of Technology (CN); Guangdong Yue Gang Water Supply Co., Ltd. (CN)

(*) Notice: Subject to any disclaimer, the term of this patent is extended or adjusted under 35 U.S.C. 154(b) by 0 days.

(21) Appl. No.: 15/758,442

(22) PCT Filed: Dec. 31, 2015

(86) PCT No.: PCT/CN2015/100076
§ 371 (c)(1),
(2) Date: Mar. 8, 2018

(87) PCT Pub. No.: WO2017/041399
PCT Pub. Date: Mar. 16, 2017

(65) Prior Publication Data
US 2018/0243716 A1      Aug. 30, 2018

(30) Foreign Application Priority Data
Sep. 9, 2015   (CN) .......................... 2015 1 0571244

(51) Int. Cl.
| | |
|---|---|
| *B01J 13/02* | (2006.01) |
| *C12R 1/32* | (2006.01) |
| *B09C 1/10* | (2006.01) |
| *C02F 3/34* | (2006.01) |
| *C12N 1/20* | (2006.01) |
| *C12N 11/10* | (2006.01) |
| *B01J 13/04* | (2006.01) |
| *C02F 101/32* | (2006.01) |

(52) U.S. Cl.
CPC .............. *B01J 13/02* (2013.01); *B01J 13/04* (2013.01); *B09C 1/10* (2013.01); *C02F 3/34* (2013.01); *C02F 3/344* (2013.01); *C12N 1/20* (2013.01); *C12N 11/10* (2013.01); *C12R 1/32* (2013.01); *C02F 2101/327* (2013.01)

(58) Field of Classification Search
CPC ....................................................... C12R 1/32
See application file for complete search history.

(56) References Cited

U.S. PATENT DOCUMENTS

2011/0217368 A1   9/2011   Prakash et al.

FOREIGN PATENT DOCUMENTS

| | | |
|---|---|---|
| CN | 102824897 A | 12/2012 |
| CN | 103523928 A | 1/2014 |
| CN | 103555612 A | 2/2014 |
| CN | 104312951 A | 1/2015 |
| CN | 105132327 A | 12/2015 |
| WO | 2010124387 A1 | 11/2010 |

OTHER PUBLICATIONS

Lu et al., "Study of phenol biodegradation using Bacillus amyloliquefaciens strain WJDB-1 immobilized in alginate-chitosan-alginate (ACA) microcapsules by electrochemical method", Biodegradation, 2012, pp. 209-219, vol. 23.
Wen-Tao et al., "Optimization of Saccharomyces cerevisiae culture in alginate-chitosan-alginate microcapsule", Biochemical Engineering Journal, 2005, pp. 151-157, vol. 25.
Zhang, "The Study of Growth and Metabolism Property of Microbe in Chitosan/Alginate Microcapsules", Chemical Technology, 2008, English-language Abstract attached.

*Primary Examiner* — Bin Shen
(74) *Attorney, Agent, or Firm* — The Webb Law Firm

(57) ABSTRACT

The present invention discloses a microcapsule material capable of reducing pollution containing polycyclic aromatic hydrocarbons, and a preparation method and application thereof. The preparation method comprises the following steps: (1) culturing *mycobacterium gilvum* CP 13 in a bacteria culture liquid to obtain a bacterial broth, wherein the *mycobacterium gilvum* CP 13 was deposited in China General Microbiological Culture Collection Center (CGMCC) on Jul. 22, 2013 with a CGMCC number of CGMCC No. 7963; and (2) applying a calcium alginate and chitosan to encapsulate the bacterial broth in a microcapsule through layer-by-layer self-assembly to produce a microcapsule material capable of reducing pollution containing polycyclic aromatic hydrocarbons. The present invention produces a microcapsule material with the microorganic activity through layer-by-layer self-assembly, which has superior adaptability to the environment and good ability to reduce pollution containing polycyclic aromatic hydrocarbons. The microcapsule material of the present invention can be used in bioremediation of industrial wastewater containing polycyclic aromatic hydrocarbons and contaminated soil containing polycyclic aromatic hydrocarbons.

4 Claims, 3 Drawing Sheets

MICROCAPSULE MATERIAL CAPABLE OF REDUCING POLLUTION CONTAINING POLYCYCLIC AROMATIC HYDROCARBON, AND PREPARATION METHOD AND APPLICATION THEREOF

CROSS-REFERENCE TO RELATED APPLICATIONS

This application is the United States national phase of International Application No. PCT/CN2015/100076 filed Dec. 31, 2015, and claims priority to Chinese Patent Application No. 201510571244.X filed Sep. 9, 2015, the disclosures of which are hereby incorporated in their entirety by reference.

BACKGROUND OF THE INVENTION

Field of the Invention

The present invention belongs to the technical field of bioremediation of environmental pollutants, in particular to the preparation of a microcapsule material for highly efficient degradation of polycyclic aromatic hydrocarbons and its application in the bioremediation of wastewater and the remediation of contaminated soil.

Description of Related Art

Polycyclic aromatic hydrocarbons, as a kind of common organic pollutants in the environment, usually refer to a class of fused ring compounds containing two or more benzene rings and arranged in a linear, angular or clustered manner, and they have bioaccumulation and environmental durability as well as carcinogenic, teratogenic and mutagenic effects (three inductions), posing a huge threat to the biosecurity and human health in nature.

Most of the polycyclic aromatic hydrocarbons in the environment are accumulated in soil. Where appropriate, they may migrate to other environmental media, expanding the range of pollution and changing the route of exposure. The polycyclic aromatic hydrocarbons in farmland, mostly caused by sewage irrigation, can be passed through crops in the form of a biological chain, and may cause damage to the human body after their accumulation therein. It is very important and urgent to rehabilitate the farmland contaminated with polycyclic aromatic hydrocarbons, especially to strengthen the rehabilitation of long-term contaminated soil.

In the polycyclic aromatic hydrocarbons that are common in the polluted environment and difficult to be degraded, since the ketone metabolites of pyrene are more toxic and mutagenic than their parents, pyrene is often used as an indicator to monitor the pollution of polycyclic aromatic hydrocarbons and a model molecule of biodegradation of other polycyclic aromatic hydrocarbons, thus becoming a representative of polycyclic aromatic hydrocarbons.

Using microbial treatment to solve the pollution problem of polycyclic aromatic hydrocarbons in the environment, having been widely accepted, has good effects, low cost, less secondary pollution and other advantages, and is thus a kind of bioremediation technology with low consumption, high efficiency and environmental safety. Currently, by artificial enrichment culture and other technologies, people have isolated many microorganisms that can degrade or transform some kind of polycyclic aromatic hydrocarbons. However, due to the vicious competition of indigenous bacteria or the change of environmental conditions, etc., free microorganisms are often difficult to adapt to the actual rehabilitation environment and cannot achieve the desired rehabilitative effects. Therefore, the development of biomaterials with high environmental adaptability and high efficiency of degrading polycyclic aromatic hydrocarbons has become one of the hot issues in the research on the abatement and remediation of polluted environment.

SUMMARY OF THE INVENTION

A purpose of the present invention is to provide a microcapsule material capable of reducing pollution containing polycyclic aromatic hydrocarbons, and a preparation method and application thereof.

In order to achieve the purpose of the present invention, the following technical solution is adopted:

A preparation method of a microcapsule material capable of reducing pollution containing polycyclic aromatic hydrocarbons is provided, comprising the following steps:

(1) culturing *mycobacterium gilvum* CP 13 in a bacteria culture liquid to obtain a bacterial broth, wherein the *mycobacterium gilvum* CP 13 was deposited in China General Microbiological Culture Collection Center (CGMCC) on Jul. 22, 2013 with a CGMCC number of CGMCC No. 7963; and (2) applying a calcium alginate and chitosan to encapsulate the bacterial broth in a microcapsule through layer-by-layer self-assembly to produce a microcapsule material capable of reducing pollution containing polycyclic aromatic hydrocarbons.

The bacteria culture liquid is nutrient broth medium having the following composition and dosage: beef extract 3 g/L, peptone 10 g/L, NaCl 5 g/L, agar 20 g/L, and a pH adjusted to 7.0-7.2.

The step (2) of encapsulating the bacterial broth in a microcapsule comprises the following steps: adding chitosan to the bacterial broth so that chitosan is deposited on the surface of bacteria, and then adding calcium alginate solution so that calcium alginate is further deposited on the surface of chitosan; repeating the operations above 2-3 times so that the bacterial broth can be encapsulated in the microcapsule.

The concentrations of chitosan and calcium alginate are both 0.1-2.0 g/L.

The microcapsule material capable of reducing pollution containing polycyclic aromatic hydrocarbons prepared by the above method is applied to degradation of polycyclic aromatic hydrocarbons in water and soil.

The polycyclic aromatic hydrocarbons are pyrene.

The microcapsule material is added in water in an amount of 0.1 g of the microcapsule material per 20 ml of water and added in soil in an amount of 2.0 g of the microcapsule material per 400 g of soil.

The present invention has the following advantages compared to the prior art:

(1) The microcapsule material of the present invention has strong adaptability to harsh environments and can be adapted to a wide range of pH and low and high temperature environments. Having superior ability to remove polycyclic aromatic hydrocarbons, the microcapsule material is capable of removing more than 81% of high concentration of polycyclic aromatic hydrocarbon pyrene contained in vegetable soil (120 mg of polycyclic aromatic hydrocarbon pyrene per kilogram of vegetable soil) within 40 days at room temperature (20° C.±5° C.), and removing more than 80% of pyrene in water (up to 50 mg/L) within 7 days, with its degradation performance not affected in strong acidity and alkalinity (pH 3-10) and at high and low temperatures (10° C.-40° C.) and under other harsh conditions. It can be used for treatment of industrial wastewater containing polycyclic aromatic hydrocarbons and soil bioremediation.

(2) The microcapsule material of the present invention consists of an environmentally safe bacterium *mycobacterium gilvum* CP13 that degrades a variety of tricyclic polycyclic aromatic hydrocarbons and tetracyclic polycyclic aromatic hydrocarbons. The microcapsule material is capable of removing a variety of polycyclic aromatic hydrocarbons in soil, suitable for southern rice field soil, vegetable soil, red soil and other soils, with the significant effect of remediating soil contaminated by polycyclic aromatic hydrocarbons.

The *mycobacterium gilvum* CP13 provided by the present invention was deposited on Jul. 22, 2013 in China General Microbiological Culture Collection Center (CGMCC) (located in Institute of Microbiology, Chinese Academy of Sciences, No. 3, 1 Beichen West Road, Chaoyang District, Beijing, P.R. China) with a CGMCC number of CGMCC No. 7963, This strain has been disclosed in a patent with a publication number CN102824897A and belongs to the prior art.

DETAILED DESCRIPTION OF THE EMBODIMENTS

The present invention will be further described below in detail with reference to specific examples; however, the embodiments of the present invention are not limited thereto, and process parameters not specifically given can be determined by referring to conventional techniques.

EXAMPLE 1

Preparation of the microcapsule material of the present invention capable of degrading polycyclic aromatic hydrocarbons A method for culturing *mycobacterium gilvum* CP13 strain of the present invention is as follows:

Respectively performing streak inoculation of the CP13 strains in beef juice peptone medium, and culturing at 28° C.-30° C. for 48 h; then respectively inoculating them into a 500 mL flask, and culturing at 30° C. and 150 r/min for 12 h; and finally inoculating them into a 5 L seed tank in accordance with an inoculum concentration of 5%, and culturing at 180 r/min, pH 7.5 and a ventilatory capacity of 5 L/min for 24 h.

Composition and dosage of the nutrient broth medium are as follows (g/L): Beef extract 3, peptone 10, NaCl 5, agar 20, and a pH adjusted to 7.0-7.2.

The specific steps are as follows: (1) Culturing *mycobacterium gilvum* CP 13 in a bacteria culture liquid to obtain a bacterial broth, (2) adding 20 ml of 0.2 g/L polycation (chitosan) to the bacterial broth so that polycation is deposited on the surface of bacteria, and then adding the same volume and concentration of polyanion (calcium alginate) solution so that polyanion is further deposited on the surface of the chitosan. Repeating the operations above 2-3 times so that the bacterial broth can be encapsulated in the microcapsule. The bacteria-immobilized microcapsules are thus prepared. They are sealed in sterile bags and stored in a refrigerator at 4° C.

EXAMPLE 2

Inoculating the microcapsule material prepared in Example 1 at a ratio of 0.1 g/20 ml to a MSM culture solution with the concentration of pyrene at 10 mg/L; taking a pyrene-containing MSM medium without the microcapsule material as a blank and placing it in a shaker at 30° C., culturing in darkness while shaking at 150 r/min, and then determining the residual amount of pyrene in the culture solution. The formulation of the MSM culture solution: 100 mg/L $(NH_4)_2SO_4$, 20 mg/L $MgSO_4 \cdot 7H_2O$, 10 mg/L $CaCl_2 \cdot 2H_2O$; trace elements: 1.2 mg/L $FeSO_4 \cdot 7H_2O$, 0.3 mg/L $MnSO_4 \cdot H_2O$, 0.3 mg/L $ZnSO_4 \cdot 7H_2O$, 0.1 mg/L $CoSO_4 \cdot 7H_2O$, 0.1 mg/L $(NH_4)_6Mo_7O_{24} \cdot 4H_2O$; phosphate buffer solution: 2.5 g/L $K_2HPO_3$, 0.77 g/L $KH_2PO_3$, pH 7.2-7.4.

Figure 1:
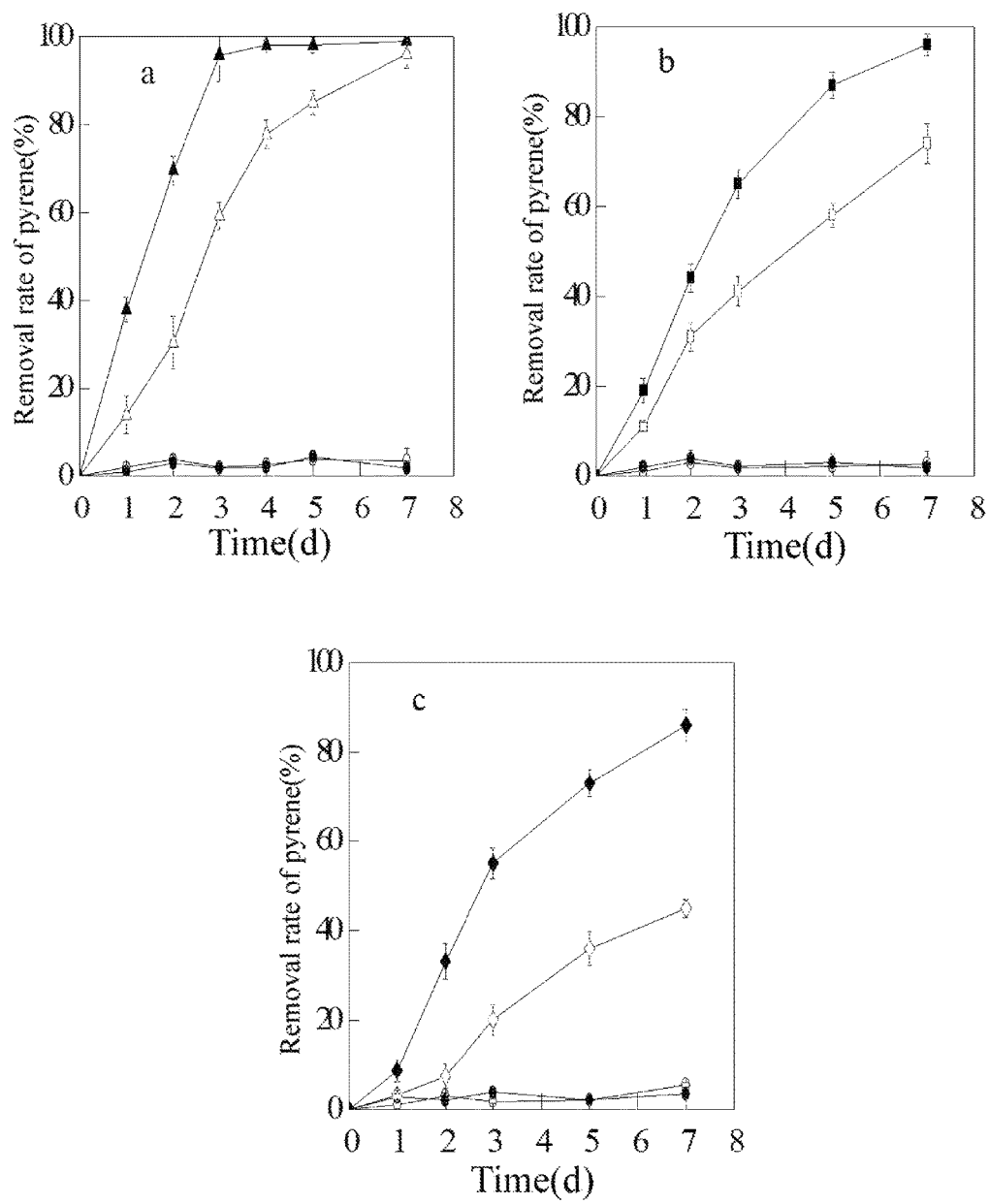
FIG. 1. Effects of different initial concentrations of pyrene on the degradation of pyrene by the microcapsule material of the present invention. (a) 10 mg/L, (b) 30 mg/L, and (c) 50 mg/L. Treatment: (○) a blank of free bacteria, (●) a blank of the microcapsule material of the present invention, (△) free bacteria, (▲) the microcapsule material of the present invention, (□) free bacteria, (■) the microcapsule material of the present invention, (◇) free bacteria, and (◆) the microcapsule material of the present invention.

As can be seen from FIG. 1, in the experimental concentration range, the efficiency of removal of PYR by the microcapsule material is higher. At the initial pyrene concentrations of 10 mg/L, 30 mg/L and 50 mg/L, respectively, the 3d removal rates are increased from 60%, 40%, 20% by the free CP13 bacteria to 95%, 65%, 55% by the microcapsule material, respectively. In the case of high concentration (such as 50 mg/L), the microcapsule material is more advantageous.

EXAMPLE 3

Figure 2:
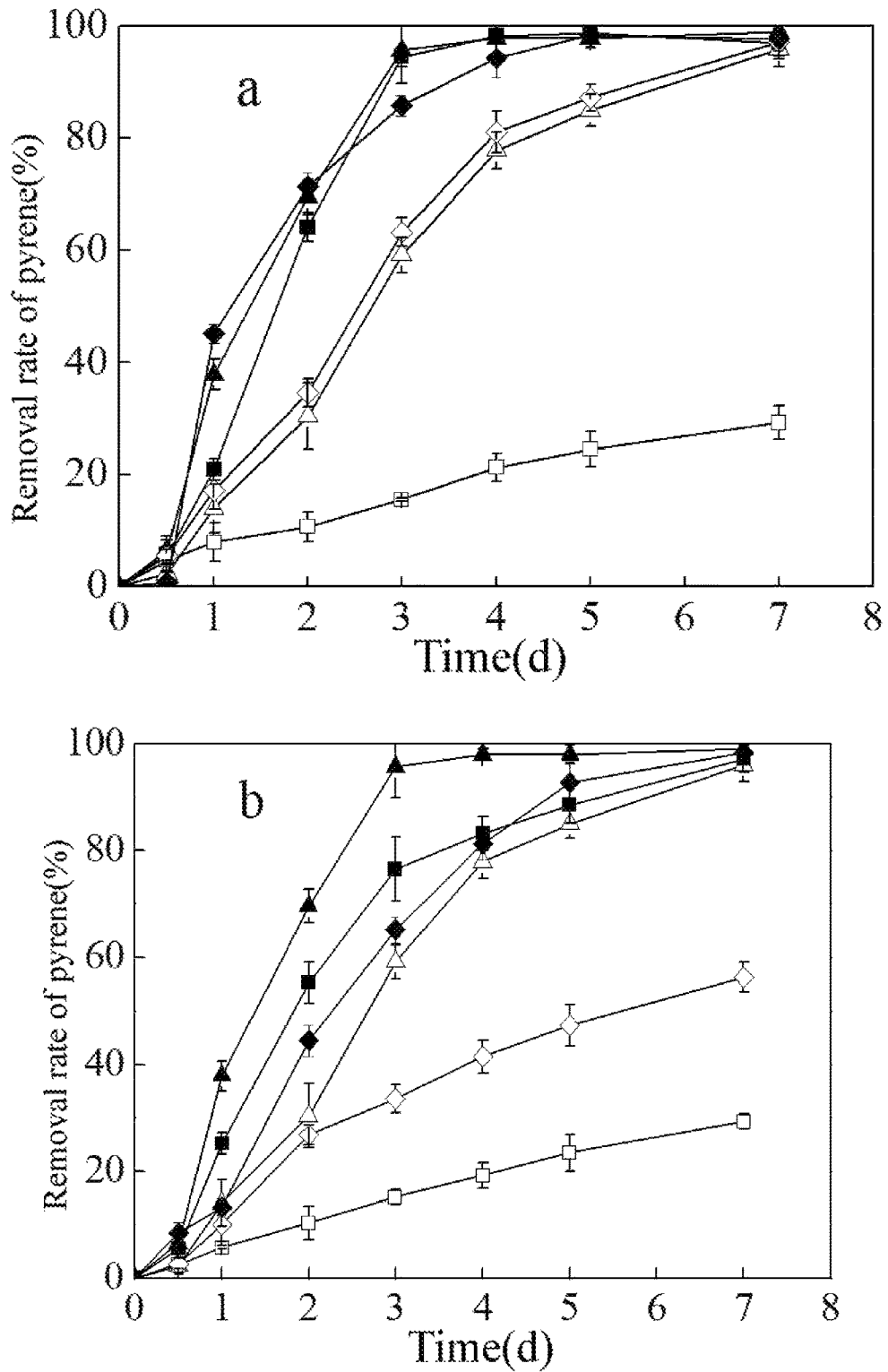
FIG. 2. Effects of different pH values (a) and different temperatures (b) on the degradation of pyrene by the microcapsule material of the present invention. Initial concentration of pyrene=10 mg/L. Treatment: (a) (△) free bacteria-pH 7, (▲) the microcapsule material of the present invention-pH 7, (□) free bacteria-pH 3, (■) the microcapsule material of the present invention-pH 3, (◇) free bacteria-pH 10, (◆) the microcapsule material of the present invention-pH 10; (b) (△) free bacteria-30° C., (▲) the microcapsule material of the present invention-30° C., (□) free bacteria-10° C., (■) the microcapsule material of the present invention-10° C., (◇) free bacteria-40° C., and (◆) the microcapsule material of the present invention-40° C.

Inoculating the microcapsule material prepared in Example 1 at a ratio of 0.1 g/20 ml to a MSM culture solution with the concentration of pyrene at 10 mg/L; taking a pyrene-containing MSM medium without the microcapsule material as a blank and free bacteria as a control and placing them in a shaker at 30° C., culturing in darkness while shaking at 150 r/min, and then determining the residual amount of pyrene in the culture solution. As can be seen from FIG. 2, the microcapsule material of the present invention can effectively degrade polycyclic aromatic hydrocarbon pyrene under the conditions of pH 3-10, Especially in the acidic case of pH 3, the removal rate of free bacteria is only 15%, while the removal rate of the microcapsule material of the present invention can still be maintained at 95% or more. As can be seen, the microcapsule material of the present invention has a broader range of pH adaptation than free bacteria. Besides, the microcapsule material of the present invention can effectively degrade polycyclic aromatic hydrocarbon pyrene at a temperature of 10° C.-40° C. Similarly, in the case of ambient temperatures as low as 10° C., the 4d removal rate by the free bacteria is only about 17%, while the 4d removal rate by the microcapsule material of the present invention can reach 80%. At 40° C., the 4d removal rate of the microcapsule material of the present invention is maintained at 80%, much higher than 40% by the free bacteria within the same duration. It can be seen that the microcapsule material of the present invention has better thermal stability than the free bacteria.

This example shows that the microcapsule material of the present invention capable of degrading polycyclic aromatic hydrocarbons can degrade pyrene well in a wide pH range of acidic, neutral and alkaline conditions and at 10° C.-40° C., ensuring its application at different pHs and in low and high temperature environments.

EXAMPLE 4

Experiment on remediation of pyrene contaminated soil by the microcapsule material of the present invention Adding 400 g of not sterile soil, to which pyrene has been added at 120 mg of pyrene per kilogram of soil, to a 500 ml beaker, and adding 2.0 g of the microcapsule material of Example 1 to the soil so that the initial inoculum is $10^7$ CFU per gram of soil. Using free CP13 as a control at the same amount of $10^7$ CFU per gram of soil, and incubating in an incubator at 30° C. Sampling to determine the residual amount of pyrene in the soil after culturing for 6 d, 10 d, 20 d, 40 d.

Figure 3:
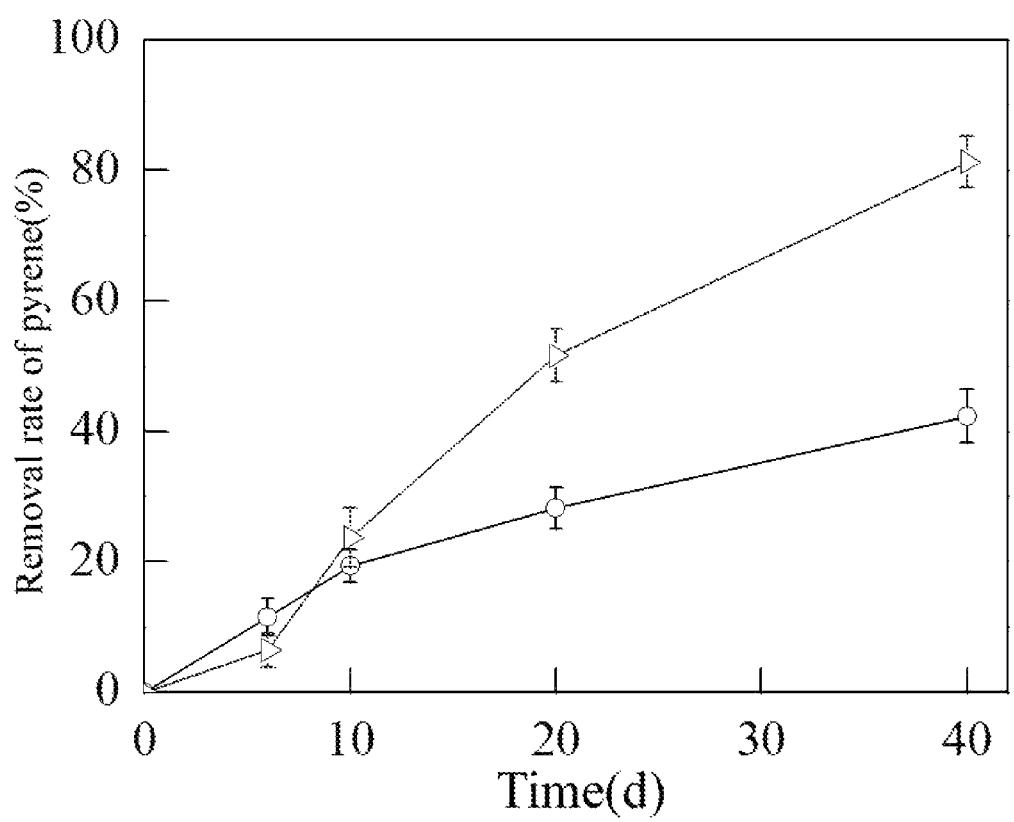
FIG. 3. Changes of the removal rate of pyrene in soil in the process of remediation of pyrene contaminated soil by the microcapsule material of the present invention. The initial concentration of pyrene=120 mg/kg. Treatment: (○) free bacteria, and (▷) the microcapsule material of the present invention.

As indicated by the results in FIG. 3, after using the microcapsule material of the present invention to treat the soil containing pyrene at 120 mg of pyrene per kilogram of soil for 40 days, the removal rate of pyrene can reach 81%, while here the degradation rate of the control using free bacteria is only 42%.

The invention claimed is:

1. A method for preparing a microcapsule material capable of reducing pollution containing polycyclic aromatic hydrocarbons, the method comprising:
    (1) culturing *mycobacterium gilvum* CP 13 in a bacteria culture liquid to obtain a bacterial broth; and
    (2) encapsulating the bacterial broth in the microcapsules by applying a calcium alginate and chitosan to the bacterial broth through layer-by-layer self-assembly to produce a microcapsule material capable of reducing pollution containing polycyclic aromatic hydrocarbons.

2. The method according to claim 1, wherein the bacteria culture liquid is nutrient broth medium, and wherein the bacteria culture liquid further comprises beef extract 3 g/L, peptone 10 g/L, NaCl 5 g/L, agar 20 g/L, and has a pH in the range of 7.0-7.2.

3. The method according to claim 1, wherein the step (2) of encapsulating the bacterial broth in the microcapsule comprise
    adding chitosan into the bacterial broth so that chitosan is deposited on a surface of bacteria,
    adding the calcium alginate into the bacterial broth so that the calcium alginate is deposited on a surface of chitosan; and
    repeating these steps 2-3 times, thereby encapsulating the bacterial broth in the microcapsules.

4. The method according to claim 3, wherein concentrations of chitosan and the calcium alginate are each in a range of 0.1-2.0 g/L.

* * * * *

UNITED STATES PATENT AND TRADEMARK OFFICE
CERTIFICATE OF CORRECTION

| | |
|---|---|
| PATENT NO. | : 10,493,418 B2 |
| APPLICATION NO. | : 15/758442 |
| DATED | : December 3, 2019 |
| INVENTOR(S) | : Chen Yang et al. |

It is certified that error appears in the above-identified patent and that said Letters Patent is hereby corrected as shown below:

On the Title Page

Column 1, Item (73) Assignees, Line 3, delete "Co.," and insert -- Co. --

In the Claims

Column 6, Line 24, Claim 3, delete "comprise" and insert -- comprises: --

Signed and Sealed this
Seventeenth Day of March, 2020

Andrei Iancu
*Director of the United States Patent and Trademark Office*